US012419955B2

(12) United States Patent
Liu et al.

(10) Patent No.: US 12,419,955 B2
(45) Date of Patent: Sep. 23, 2025

(54) METHOD FOR EFFICIENTLY INFECTING HUMAN NATURAL KILLER CELLS AND OTHER IMMUNE CELLS WITH PSEUDOVIRUS

(71) Applicant: Beijing Gene MINK Biotechnology CO.LTD, Beijing (CN)

(72) Inventors: Yongfeng Liu, Beijing (CN); Zhihua Lu, Beijing (CN)

(73) Assignee: Beijing Gene MINK Biotechnology CO.LTD, Beijing (CN)

( * ) Notice: Subject to any disclaimer, the term of this patent is extended or adjusted under 35 U.S.C. 154(b) by 0 days.

(21) Appl. No.: 18/900,968

(22) Filed: Sep. 30, 2024

(65) Prior Publication Data

US 2025/0018035 A1    Jan. 16, 2025

Related U.S. Application Data

(63) Continuation of application No. PCT/CN2023/112838, filed on Aug. 14, 2023.

(30) Foreign Application Priority Data

Apr. 28, 2023  (CN) .......................... 202310476442.2
May 4, 2023    (CN) .......................... 202310489784.8

(51) Int. Cl.
| | | |
|---|---|---|
| A61K 39/00 | (2006.01) | |
| A61K 40/11 | (2025.01) | |
| A61K 40/15 | (2025.01) | |
| A61K 40/31 | (2025.01) | |
| A61K 40/42 | (2025.01) | |
| C07K 14/725 | (2006.01) | |
| C07K 16/28 | (2006.01) | |
| C12N 15/86 | (2006.01) | |

(52) U.S. Cl.
CPC .......... *A61K 40/4202* (2025.01); *A61K 40/11* (2025.01); *A61K 40/15* (2025.01); *A61K 40/31* (2025.01); *C07K 14/7051* (2013.01); *C07K 16/2878* (2013.01); *C12N 15/86* (2013.01); *C12N 2710/16143* (2013.01)

(58) Field of Classification Search
None
See application file for complete search history.

(56) References Cited

U.S. PATENT DOCUMENTS 11,311,609 B2 *  4/2022  Bradner ............... C07D 495/04

FOREIGN PATENT DOCUMENTS

| CN | 106029873 A | 10/2016 |
|---|---|---|
| CN | 115340999 A | 11/2022 |
| CN | 115820742 A | 3/2023 |

* cited by examiner

*Primary Examiner* — Robert M Kelly

(57) ABSTRACT

The present disclosure belongs to the field of biotechnology, and specifically relates to a method for efficiently infecting human natural killer (NK) cells and other immune cells with a pseudovirus. Specifically, a viral transfection system provided in the present disclosure has an envelope plasmid with a protein having an X-Y-Z structure. The X is an extracellular (ex) structure of a gibbon ape leukemia virus (GALV) envelope glycoprotein, the Y is a transmembrane (TM) structure of the GALV envelope glycoprotein, and the Z is an intracellular segment portion of a murine virus gene.

7 Claims, 19 Drawing Sheets

Specification includes a Sequence Listing.

METHOD FOR EFFICIENTLY INFECTING HUMAN NATURAL KILLER CELLS AND OTHER IMMUNE CELLS WITH PSEUDOVIRUS

CROSS-REFERENCE TO RELATED APPLICATIONS

This application is a continuation of PCT/CN2023/112838, filed on Aug. 14, 2023; claims priority of Chinese Patent Application No. 202310489784.8, filed on May 4, 2023 and priority of Chinese Patent Application No. 202310476442.2, filed on Apr. 28, 2023, the entire contents of which are incorporated herein by reference.

SEQUENCE LISTING

The instant application contains a Sequence Listing with 3 sequence, which has been submitted electronically in XML format and is hereby incorporated herein by reference in its entirety. Said XML copy, created on Sep. 27, 2024, is named HBJS-US-1-29_Seq listings.xml, and is 4.23 kbytes in size.

TECHNICAL FIELD

The present disclosure belongs to the field of biotechnology, and specifically relates to a method for efficiently infecting human natural killer (NK) cells and other immune cells with a pseudovirus.

BACKGROUND

NK cells in the innate immune system possess excellent killing capabilities and only express pattern recognition receptors, allowing for allogeneic transfusion without significant graft-versus-host disease (GVHD). The preparation of chimeric antigen receptor (CAR)-NK cell products based on NK cells enables large-scale production and allogeneic transfusion, making it a next-generation cell therapy product that is expected to replace existing CAR-T products.

Currently, the main gene delivery methods employed to prepare CAR-NK products are viral transduction systems, including lentiviral systems, retroviral systems, and methods using transposons/transposase by a few companies. All of these methods face a common technical challenge: the efficiency of gene delivery is too low and unstable. Most CAR-NK cell products have a CAR positive rate of only about 10%, failing to meet the minimum requirement for cell-based products: a CAR positive rate≥30%. Furthermore, as CAR-NK cells are subsequently expanded, the CAR positive rate further declines, resulting in only 1-2% positive rate. Therefore, optimizing gene delivery methods to improve the transduction efficiency of NK cells and obtain a high proportion of CAR-NK products is currently a key focus and challenge in research and development.

Additionally, according to literature reports, the vesicular stomatitis virus-G (VSV-G) or myeloid differentiation protein-2 G (MD2.G) envelope proteins used in the lentiviral system can inhibit NK cell proliferation and even induce NK cell apoptosis, leading to a continuous decline in the positive rate of CAR-NK cells. Ultimately, the positive rate of CAR-NK cells can drop to 1-2%, failing to meet the requirements for preparing CAR-NK cell products.

SUMMARY

To solve the above technical problems, the present disclosure constructs a new viral envelope protein (Envelope) through bioinformatics analysis and experimental screening, and then forms a new pseudovirus and a viral transduction system. Instead of relying on the low-density lipoprotein receptor (LDLR) to infect NK cells, this new pseudovirus infects cells via another receptor, SLC20A1, which is highly expressed on immune cells, and delivers a target gene to NK cells. Gene delivery using this pseudovirus results in CAR-NK cells with a transduction rate of up to 90%. CAR-NK cells can be expanded up to 2500-fold without inhibiting the expansion of NK cells while maintaining a high positive rate.

Specifically, the present disclosure provides the following technical solutions.

Protein

In one aspect, the present disclosure provides a protein, the protein having an X-Y-Z structure. The X is an extracellular (ex) structure of a gibbon ape leukemia virus (GALV) envelope glycoprotein, the Y is a transmembrane (TM) structure of the GALV envelope glycoprotein, and the Z is an intracellular segment portion of a murine virus gene (MEVc).

Preferably, the ex structure of the GALV envelope glycoprotein has at least 80%, 85%, 90%, 91%, 92%, 93%, 94%, 95%, 96%, 97%, 98%, or 99% sequence identity to SEQ ID NO.1, or, has a substitution, deletion, or addition of 1, 2, 3, 4, 5, 6, 7, 8, 9, or 10 amino acids compared to SEQ ID NO.1.

Preferably, the TM structure of the GALV envelope glycoprotein has at least 80%, 85%, 90%, 91%, 92%, 93%, 94%, 95%, 96%, 97%, 98%, or 99% sequence identity to SEQ ID NO.2, or, has a substitution, deletion, or addition of 1, 2, 3, 4, 5, 6, 7, 8, 9, or 10 amino acids compared to SEQ ID NO.2.

Preferably, the Z has at least 80%, 85%, 90%, 91%, 92%, 93%, 94%, 95%, 96%, 97%, 98%, or 99% sequence identity to SEQ ID NO.3, or, has a substitution, deletion, or addition of 1, 2, 3, 4, 5, 6, 7, 8, 9, or 10 amino acids compared to SEQ ID NO.3.

More preferably, an amino acid sequence of the X is shown in SEQ ID NO.1.

More preferably, an amino acid sequence of the Y is shown in SEQ ID NO.2.

More preferably, an amino acid sequence of the Z is shown in SEQ SEQ ID.3. More specifically, the MEVc of the present disclosure is the first 17 amino acids of the intracellular segment of GenBank:AH002056.2 (*Mus musculus* endogenous virus endogenous Moloney-like murine retrovirus N-myc and envpolypeptide genes).

That is, most preferably, a sequence of the protein in the present disclosure is a protein (or peptide, polypeptide, peptide fragment) formed by sequentially ligating SEQ ID NO.1, SEQ ID NO.2 and SEQ ID NO.3.

It is well known in the art that the structure or sequence of a protein can be altered without adversely affecting its activity and function. For example, one or more conservative amino acid substitutions can be introduced into an amino acid sequence of a protein without negatively impacting the activity and/or three-dimensional structure of the protein molecule. Those skilled in the art are aware of examples and methods for implementing conservative amino acid substitutions. Specifically, as long as the substitution does not lead to the inactivation of the protein's biological activity, a conservative substitution where one amino acid is replaced by another falls within the scope of the present disclosure. Furthermore, it is well known in the art that one or more amino acid residues can be altered (replaced, deleted, truncated, or inserted) from an N and/or C terminal of a protein while still retaining its functional activity.

As used herein, the term "identity" refers to the matching of sequences between two polypeptides or two nucleic acids. When a position in the two compared sequences is occupied by the same base or amino acid monomer (for example, a lysine occupies a position in each of the two polypeptides), the various molecules are identical at that position.

In a specific embodiment, the protein of the present disclosure is named QMV, and a viral transduction system using QMV as an envelope protein is also referred to as a QMV viral transduction system.

Fusion Protein

In another aspect, the present disclosure provides a fusion protein containing the above protein.

Preferably, the fusion protein may further include other modified portions, the modified portions including epitope tags, detectable marks, nuclear localization signal (NLS) sequences, and so on.

Specifically, the epitope tags are well known to those of skill in the art, including, but not limited to, His, V5, FLAG, HA, Myc, VSV-G, Trx, and so on, and those of skill in the art may select any suitable epitope tags (e.g., purification, detection, or tracing); and the detectable markers include reporter gene sequences, or, fluorescent dyes, such as fluorescein isothiocyanate (FITC) or 4',6-diamidino-2-phenylindole (DAPI), the reporter gene sequences being well known to those of skill in the art, examples of which include, but are not limited to, GST, HRP, CAT, GFP, HcRed, DsRed, CFP, YFP, BFP, and so on.

The protein or the fusion protein of the present disclosure are not limited by the manner in which they are produced, for example, they can be produced by genetic engineering (recombinant technology) or by chemical synthesis.

Nucleic Acid Molecule

In another aspect, the present disclosure provides a nucleic acid molecule, the nucleic acid molecule containing a nucleic acid sequence encoding a protein or a fusion protein of the present disclosure.

More preferably, the nucleic acid molecule is a nucleic acid sequence encoding a protein or a fusion protein of the present disclosure.

It is well known in the art that different organisms exhibit variations in the usage frequency of degenerate codons in the translation process. Throughout evolution, a set of commonly used codons (codon preference) has been developed that is adapted to each organism. Codon optimization involves using genetic engineering techniques to adjust synonymous codons of a gene according to the codon preference of a host, aiming to eliminate rare codons and optimize related parameters such as a messenger ribonucleic acid (mRNA) secondary structure and Motif, thereby improving translation efficiency. The coding sequences obtained through codon optimization to enhance expression levels in different hosts fall within the protective scope of the nucleic acid molecule of the present disclosure.

In one embodiment, the nucleic acid molecule is codon-optimized for expression in prokaryotic cells. In another embodiment, the nucleic acid molecule is codon-optimized for expression in eukaryotic cells. The eukaryotic cell includes human or other animal cells.

The terms "nucleic acid", "nucleic acid molecule", "nucleic acid sequence", "polynucleotide", "oligonucleotide", "coding nucleic acid", and "nucleotide sequence" are used interchangeably in this specification to mean a precise nucleotide sequence.

Vector

In another aspect, the present disclosure further provides a vector, the vector expressing a foregoing protein or fusion protein, or, the protein containing a foregoing nucleic acid molecule.

Preferably, the vector further contains a regulatory element common in the art.

Preferably, the regulatory element includes any one or more of the followings: an enhancer, a transposon, a promoter, a terminator, a lead sequence, a polyadenylate sequence, and a marker gene.

Preferably, a cytomegalovirus (CMV) is used as a promoter in specific embodiments of the present disclosure. The CMV promoter is a strong promoter found in CMV, the function and sequence of which are well known in the art.

In a specific embodiment, the vector may be referred to as an envelope plasmid in a viral transduction system, which in combination with other vectors expressing viral genes becomes a viral transduction system to realize viral transduction functions.

Vector Composition

In another aspect, the present disclosure further provides a vector composition, the vector composition including a first vector component and a second vector component. The first vector component includes a vector as described above, and the second vector component contains a vector or vector composition containing nucleic acids encoding proteins required for the assembly of a lentivirus, or, the second vector component expresses proteins required for the assembly of the lentivirus.

Preferably, the protein required for the assembly of the lentivirus includes at least one of regulator of expression of virion protein (REV), group specific antigen (GAG), and polymerase (POL).

Preferably, the protein required for the assembly of the lentivirus includes REV, GAG and POL.

Preferably, the second vector component may further include nucleic acids encoding any one or more of the following genes: a regulatory gene tat, accessory genes vpr, vif, vpu, and nef, a long terminal repeat (LTR) sequence, a viral packaging signal, and so on.

Specifically, the second vector component may be a plasmid or a plurality of plasmids intended to express REV, GAG and POL, and nucleic acids encoding REV, GAG and POL may be ligated to the same vector or to different vectors.

More specifically, the second vector component may be a packaging plasmid in a commercially available lentivirus transduction product. The composition of the second vector component is readily determinable according to the composition of the lentiviral transduction system.

In a specific embodiment, the second vector component includes a packaging plasmid 1 and a packaging plasmid 2, the packaging plasmid 1 containing nucleic acids encoding GAG and POL, and the packaging plasmid 2 containing nucleic acids encoding REV.

In another specific embodiment, the second vector component is 1 plasmid, the plasmid containing nucleic acids encoding REV, GAG and POL.

As well known in the art, the GAG gene encodes viral core proteins such as a nucleocapsid protein (p7), an endosomal protein (p17), and a capsid protein (p24), the POL gene encodes viral replication-associated enzymes, and REV is an RNA-binding protein that ensures expression of the gene. The functions of the above genes and their specific sequences are well known and readily available in the art.

In a specific embodiment, the vector composition can be referred to as a system (viral system, viral transduction system, and viral packaging system), which has the function of producing viral particles.

More preferably, the vector composition includes the following plasmids:
1) an expression plasmid (containing a coding sequence of a target gene or a protein expressing the target gene),
2) a packaging plasmid 1 (containing coding sequences of GAG and POL or expressing GAG and POL),
3) a packaging plasmid 2 (containing a coding sequence of REV or expressing REV), and
4) an envelope plasmid (the aforementioned vector).

Preferably, the packaging plasmid 1, the packaging plasmid 2, and the envelope plasmid each independently includes a CMV promoter.

Composition

In another aspect, the present disclosure provides a composition, the composition containing the above vector composition as well as a transfection reagent.

Specifically, the transfection reagent has the effect of introducing a target gene (which in the present disclosure may be a viral vector) into target cells. For example, the transfection reagent may be a commercially available product, such as Lipofectamine2000 and similar products thereof (thermofisher), Lipo293F™ transfection reagent and similar products thereof (deyotime), X-tremeGENE™360DNA Transfection Reagent and similar products thereof (Roche), high efficiency nucleic acid transfection kit (L3170, Solarbio), LipoJet™ transfection kit (Ver.II), and so on. Or, the transfection reagent may be various types of polyethylenimine (PEI) and derivatives thereof, and the PEI and derivatives thereof may be used as a single component, or as a mixture of components.

Host Cells

In another aspect, the present disclosure further provides host cells, the host cells expressing a forgoing protein or fusion protein, or, the host cells containing a forgoing nucleic acid molecule, vector or vector composition.

Preferably, the host cell includes prokaryotic cells and eukaryotic cells.

Preferably, the eukaryotic cells include lower eukaryotic cells and higher eukaryotic cells.

Preferably, the higher eukaryotic cells include animal cells and mammalian cells.

Preferably, the mammalian cells include immune cells, stem cells, somatic cells, blood cells and so on.

Preferably, the immune cells include T cells (T lymphocytes), B cells (B lymphocytes), NK cells (NK lymphocytes), NKT cells, dendritic cells, plasma cells, granulocytes, mast cells, antigen-presenting cells, mononuclear phagocytes, and so on.

Preferably, the stem cells include embryonic stem cells and adult stem cells.

Preferably, the stem cells are derived from embryo, bone marrow, peripheral blood, umbilical cord and umbilical cord blood.

Preferably, the stem cells include isolated stem cells or cells induced in vitro to possess pluripotency, such as induced pluripotent stem cells (iPSC) and extended pluripotent stem cells (EPSC).

It is well known in the art that the stem cells, which are called "universal cells", can be categorized into embryonic stem cells and adult stem cells according to their stages of development. According to the developmental potential of stem cells, they can be classified into totipotential stem cell, pluripotent stem cells and monopotent stem cells. According to the functions of adult stem cells, they can be classified into neural stem cells, hematopoietic stem cells, bone marrow mesenchymal stem cells, skin stem cells, adipose-derived stem cells, and so on.

Preferably, the mammal is a human being and the cells are human cells.

In a specific embodiment, the host cells may be cells used in the process of preparing a viral liquid. The host cells are transfected by a viral transduction system to express viral particles that can thus be applied to subsequent viral transduction.

Cells commonly used in serving as host cells for use in the preparation of viral liquid include various cell lines, such as 293 cells, 293T cells, 293FT cells, 293LTV cells, 293F cells, 293EBNA cells, and other clones isolated from 293 cells; and SW480 cells, u87MG cells, HOS cells, C8166 cells, MT-4 cells, Molt-4 cells, HeLa cells, HT1080 cells, and TE671 cells.

Preferably, the cell line used in the preparation of the viral liquid of the present disclosure is HEK293T (also known as 293T, a human embryonic kidney cell-derived cell line).

Method for Preparing Viral Liquid

In another aspect, the present disclosure further provides a method for preparing a viral liquid, the method including the step of transfecting a vector composition into cells (or host cells): the vector composition including a first vector component and a second vector component. The first vector component includes a vector as described above, and the second vector component contains a vector or vector composition containing nucleic acids encoding proteins required for the assembly of a lentivirus, or, the second vector component expresses proteins required for the assembly of the lentivirus.

Preferably, the protein required for the assembly of the lentivirus includes REV, GAG and POL.

Preferably, the second vector component may further include nucleic acids encoding any one or more of the following genes: a regulatory gene tat, accessory genes vpr, vif, vpu, and nef, an LTR sequence, a viral packaging signal, and so on.

Specifically, the second vector component may be a plasmid or a plurality of plasmids intended to express REV, GAG and POL, and nucleic acids encoding REV, GAG and POL may be ligated to the same vector or to different vectors.

In a specific embodiment, the second vector component includes a packaging plasmid 1 and a packaging plasmid 2, the packaging plasmid 1 containing nucleic acids encoding GAG and POL, and the packaging plasmid 2 containing nucleic acids encoding REV.

In another specific embodiment, the second vector component is 1 plasmid, the plasmid containing nucleic acids encoding REV, GAG and POL.

More preferably, the vector composition includes the following plasmids:
1) an expression plasmid (containing a coding sequence of a target gene or a protein expressing a target gene),
2) a packaging plasmid 1 (containing coding sequences of GAG and POL or expressing GAG and POL),
3) a packaging plasmid 2 (containing a coding sequence of REV or expressing REV), and
4) an envelope plasmid.

More preferably, the method further includes the step of purifying the viral liquid.

More preferably, when preparing a viral liquid containing a specific target gene, it is necessary to transfect a vector expressing the target gene into the cells.

Preferably, the target gene of the present disclosure may be a coding sequence of any one of genes. For example, the target gene includes a nucleic acid encoding an antibody, a CAR or a functional protein.

It is well known in the art that the term "CAR" may include an antigen-binding structural domain (e.g., an antibody targeting a cancer therapeutic target), a TM structural domain, a co-stimulatory domain, and an intracellular signal transduction structural domain. With the development of CAR technology, it is also possible to introduce one or more co-stimulatory molecules or other components to the CAR structure. Regardless of structural variations, the genes encoding the above CARs or their similar structures can be used as target genes as described in the present disclosure.

As is well known in the art, the transfection method for transfecting cells with the vector composition is conventional. As in the present disclosure, the transfection method used is to promote transfection by PEI, and the use of PEI is well known in the art. Specifically, a volume-to-mass ratio of PEI to the vector composition used in the present disclosure is 3:1, which may be determined according to the specific PEI type in a manner known in the art. The reagent that may be used in the transfection method, such as the aforementioned finished transfection reagent or self-formulated reagents for promoting transfection, is known in the art.

Viral Particles

In another aspect, the present disclosure provides viral particles, the viral particles containing a protein of the present disclosure and proteins required for the assembly of a lentivirus.

Preferably, the protein required for the assembly of the lentivirus includes REV, GAG and POL.

Preferably, the protein required for the assembly of the lentivirus further includes any one or more of the followings: a regulatory gene tat, auxiliary genes vpr, vif, vpu, and nef, and so on.

Preferably, the viral particles further contain a target protein (a protein encoded by a target gene).

Preferably, the target gene of the present disclosure may be a coding sequence of any one of genes. For example, the target gene includes a nucleic acid encoding an antibody, a CAR or a functional protein. That is, the target protein includes an antibody, CAR or a functional protein.

In a specific embodiment, the viral particle is the main product prepared by the aforementioned method for preparing a viral liquid.

Method for Preparing Cells Expressing Target Gene

In another aspect, the present disclosure provides a method for preparing target cells expressing a target gene. The method includes the steps of transfecting cells with a vector composition, collecting a viral liquid, and contacting the viral liquid with the target cells.

In a specific embodiment, the cell and the target cell are/are not the same cell, and the specific cell type thereof may be self-independently selectable from any one of a number of suitable cells, the selection of the suitable cell being in a manner well known in the art.

The vector composition includes a first vector component and a second vector component. The first vector component includes a vector as described above, and the second vector component contains a vector or vector composition containing nucleic acids encoding proteins required for the assembly of a lentivirus, or, the second vector component expresses proteins required for the assembly of the lentivirus.

Preferably, the protein required for the assembly of the lentivirus includes REV, GAG and POL.

Preferably, the second vector component may further include nucleic acids encoding any one or more of the following genes: a regulatory gene tat, accessory genes vpr, vif, vpu, and nef, an LTR sequence, a viral packaging signal, and so on.

Specifically, the second vector component may be a plasmid or a plurality of plasmids intended to express REV, GAG and POL, and nucleic acids encoding REV, GAG and POL may be ligated to the same vector or to different vectors.

In a specific embodiment, the second vector component includes a packaging plasmid 1 and a packaging plasmid 2, the packaging plasmid 1 containing nucleic acids encoding GAG and POL, and the packaging plasmid 2 containing nucleic acids encoding REV.

In another specific embodiment, the second vector component is 1 plasmid, the plasmid containing nucleic acids encoding REV, GAG and POL.

More preferably, the vector composition includes the following plasmids:
1) an expression plasmid (containing a coding sequence of a target gene or a protein expressing a target gene),
2) a packaging plasmid 1 (containing coding sequences of GAG and POL or expressing GAG and POL),
3) a packaging plasmid 2 (containing a coding sequence of REV or expressing REV), and
4) an envelope plasmid (the aforementioned vector).

More preferably, the expression plasmid, the packaging plasmid 1, the packaging plasmid 2 and the envelope plasmid are in a mass ratio of 2:1:1:1 in specific embodiments of the present disclosure, and the mass ratio is readily obtainable by a person skilled in the art by conventional methods.

More preferably, the method further includes the steps of purifying a viral liquid.

In a specific embodiment, the method may also be referred to as a method for using the aforementioned viral particles.

In another aspect, the present disclosure provides target cells prepared by the above-described method for preparing target cells expressing a target gene, that is, the present disclosure provides target cells expressing a target gene by transduction with a protein and a viral vector of the present disclosure.

In another aspect, the present disclosure provides an application of the above-described target cells in the preparation of a drug.

Preferably, the drug is used for the treatment of cancer, specifically including cells and drugs used in immunotherapy and cell therapy.

As used in specific embodiments, the present disclosure prepares NK cells expressing a CAR targeting a B cell maturation antigen (BCMA), thereby obtaining a drug for the treatment of BCMA-related cancer.

Application

In another aspect, the present disclosure provides applications of a protein, a fusion protein, a nucleic acid molecule, a vector, a vector composition, a composition, and host cells of the present disclosure in the preparation of viral particles expressing a target gene.

In another aspect, the present disclosure provides applications of a protein, a fusion protein, a nucleic acid molecule, a vector, a vector composition, a composition, and host cells of the present disclosure in causing target cells to express a target gene by viral transduction (preparation of cells expressing the target gene).

Preferably, the target cells include immune cells, stem cells and so on.

Preferably, the immune cells include T cells (T lymphocytes), B cells (B lymphocytes), NK cells (NK lymphocytes), NKT cells, dendritic cells, plasma cells, granulocytes, mast cells, antigen-presenting cells, mononuclear phagocytes, and so on.

Preferably, the immune cells include isolated immune cells or immune cells induced and differentiated from stem cells.

Preferably, the stem cells include embryonic stem cells and adult stem cells.

Preferably, the stem cells are derived from embryo, bone marrow, peripheral blood, umbilical cord and umbilical cord blood.

It is well known in the art that the stem cells, which are called "universal cells", can be categorized into embryonic stem cells and adult stem cells according to their stage of development. According to the developmental potential of stem cells, they can be classified into totipotential stem cell, pluripotent stem cells and monopotent stem cells. According to the functions of adult stem cells, they can be classified into neural stem cells, hematopoietic stem cells, bone marrow mesenchymal stem cells, skin stem cells, adipose-derived stem cells, and so on.

Preferably, the target gene of the present disclosure may be a coding sequence of any one of genes. For example, the target gene includes a nucleic acid encoding an antibody, a CAR or a functional protein.

The "antibody" or "CAR" described in the present disclosure can target different sites, including hematologic tumor targets: BCMA, CD19, CD20, CD123, CD22, CD3D, CD3E, CD7CLEC12AGPRC5D, CD138, CD30, CD33, CD38, CD3E, CD79BSLAMF7, CD10, CD117, CD37, CD4, CD5, CD56, CD72, CD79A, CD99, Flt-3, LILRA3, LILRB4, and SLAMF3; solid tumor targets: Her2, MSLN, B7-H3, CLDN18, EGFR, GPC3, KRAS(G12D), CA9, CEA, EGFRvIII, EphA2, ERBB3, ERBB4, FAP, GUCY2C, IL13RA2, MUC1, PD-1, PSMA, VEGFR2, AFP, AXL, CD133, CD147, CD171, CD80, CD86, c-Met, DLL4, EpCAM, Nectin-4, Podoplanin, ROBO1, ROR2, and SSTR2; and target both solid and non-solid tumors: FOLR1, ROR1, CD70, NKG2D, PD-L1, and SIRP alpha. In specific embodiments of the present disclosure, a CAR structure centered on a monoclonal antibody that targets (specifically binds to) BCMA is constructed as a target gene for validation.

The term "antibody" as used in the present disclosure refers to an immunoglobulin molecule that immunoreacts with a specific antigen, denotes a protein molecule that acts as a receptor for the specific recognition of an antigen, and may include polyclonal antibodies, monoclonal antibodies, whole antibodies, and antibody fragments. In addition, the term may include chimeric antibodies (e.g., humanized murine antibodies), bivalent or bispecific molecules (e.g., bispecific antibodies), double antibodies, triple antibodies, and quadruple antibodies.

DETAILED DESCRIPTION

Figure 1A:
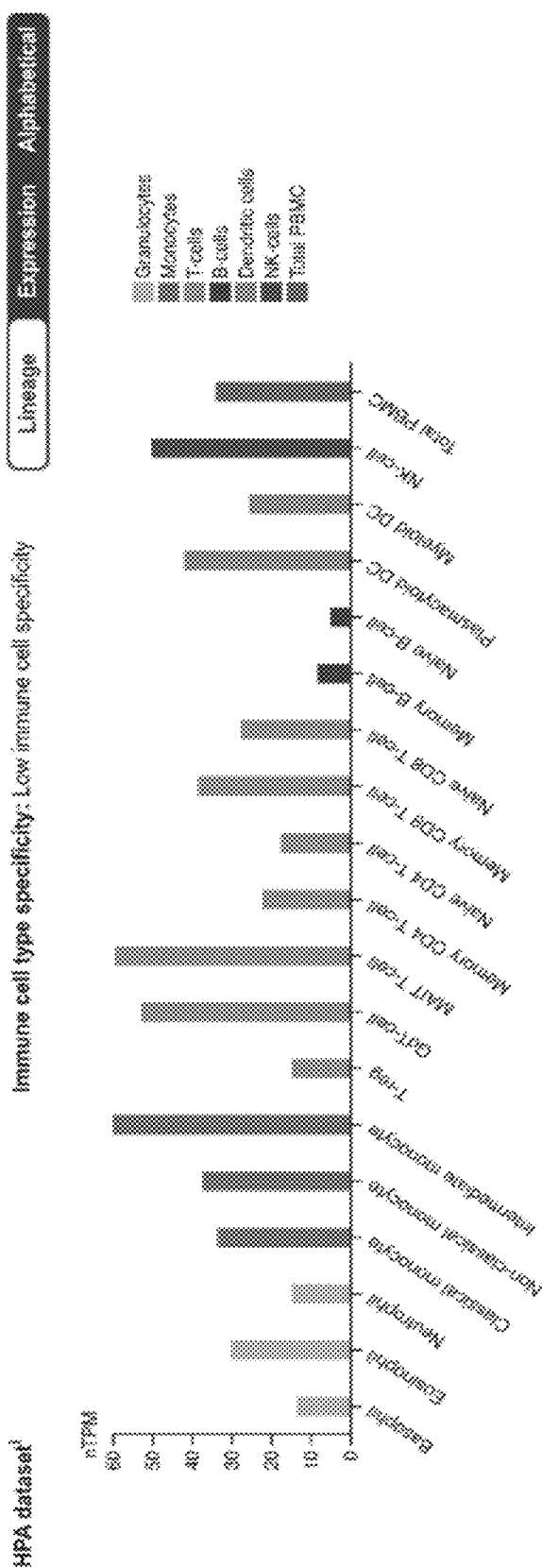
FIG. 1 is a graph showing the results of the analysis of the expression of SLC20A1 in blood cells.
Figure 1B:
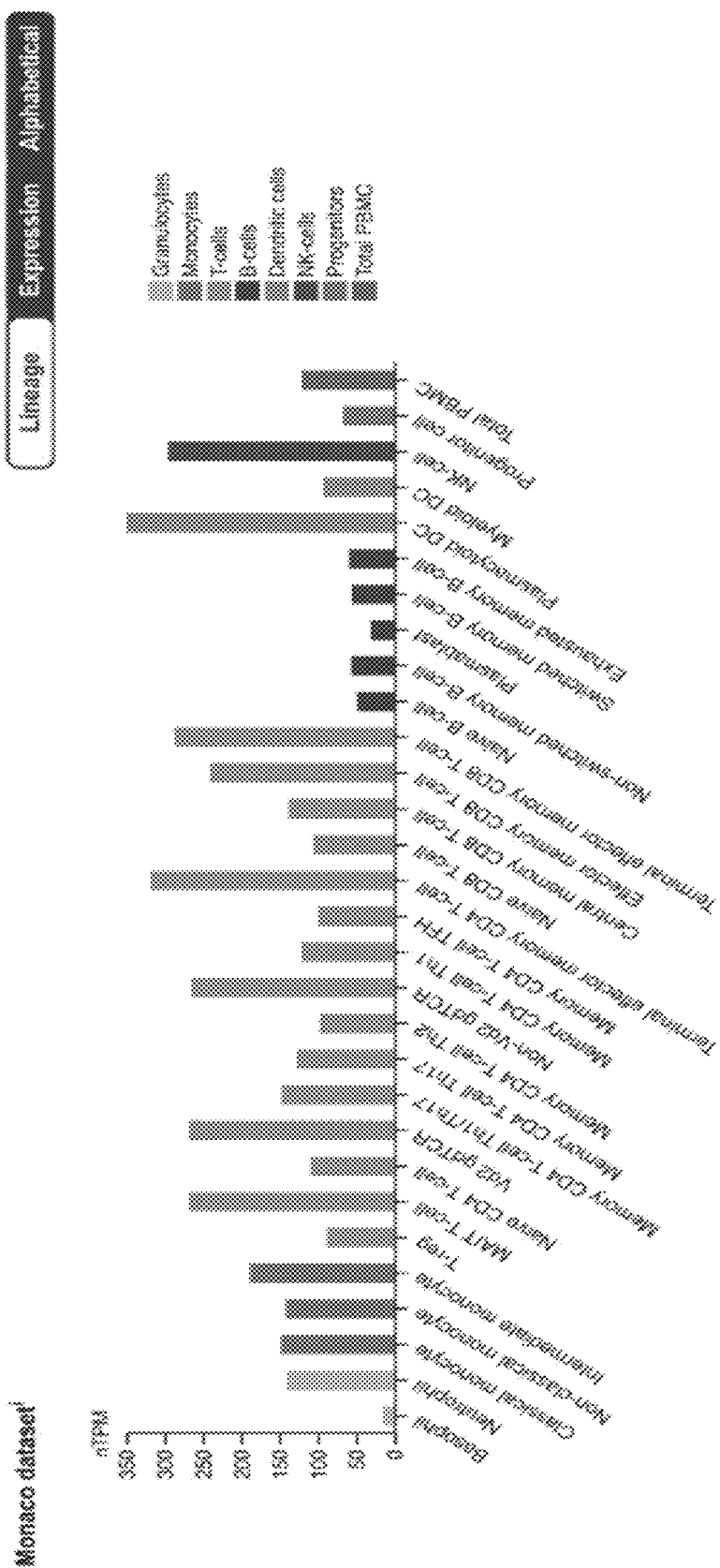
Figure 1C:
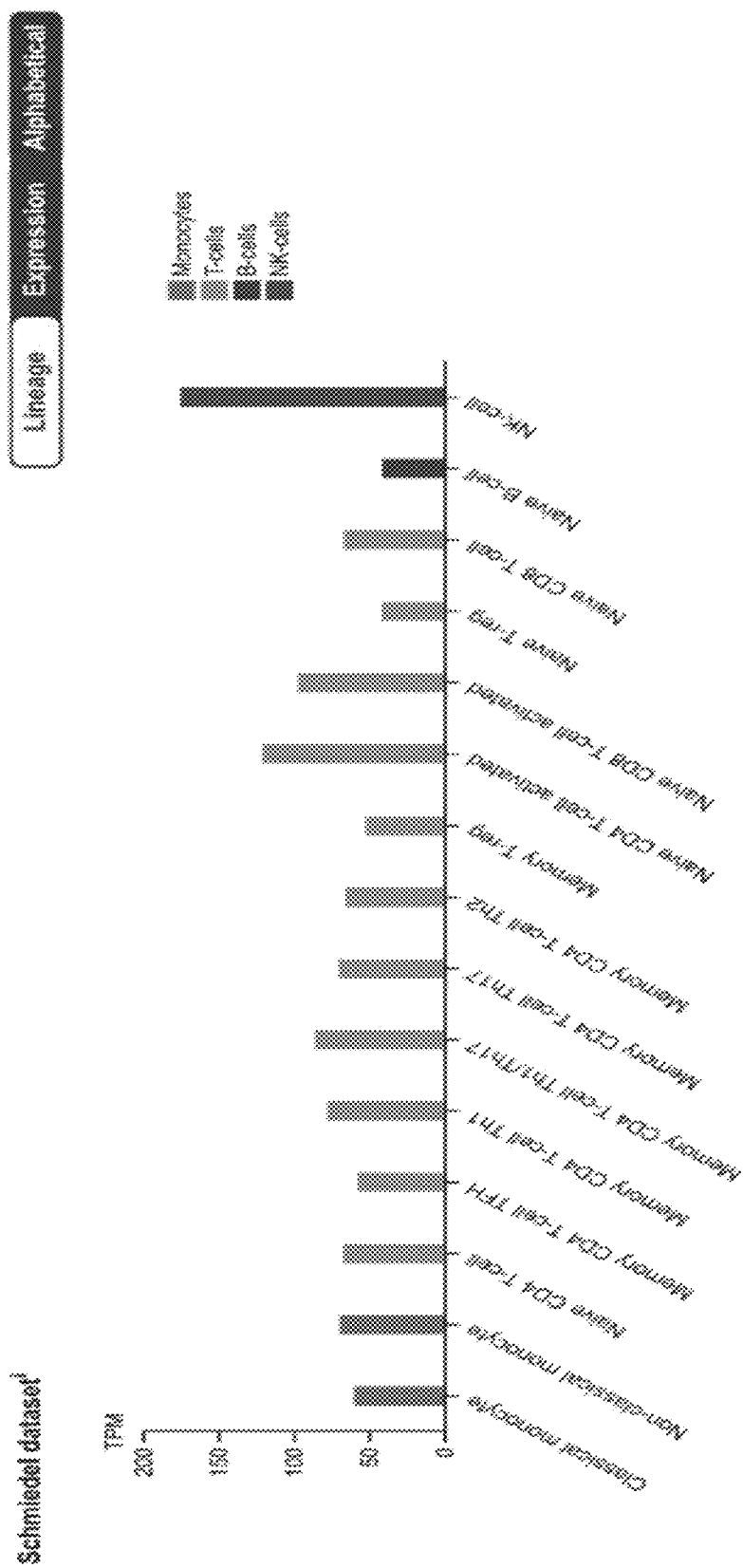
Figure 2A:
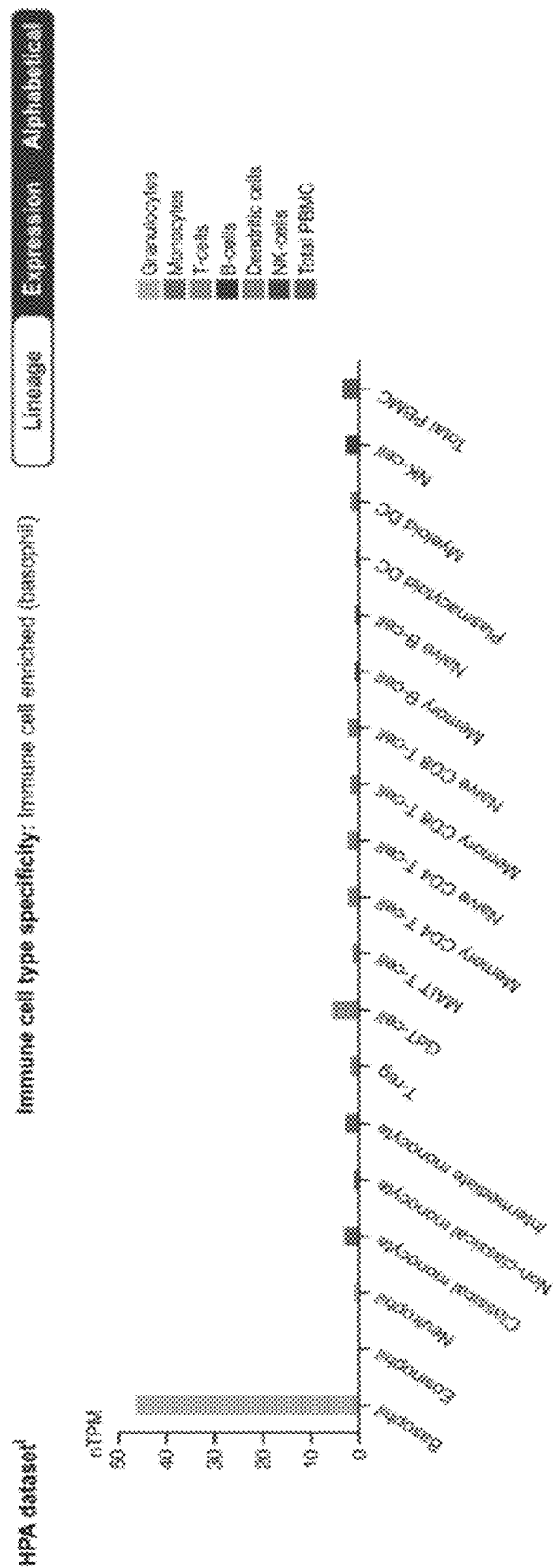
FIG. 2 is a graph showing the results of the analysis of the expression of LDLR in blood cells.
Figure 2B:
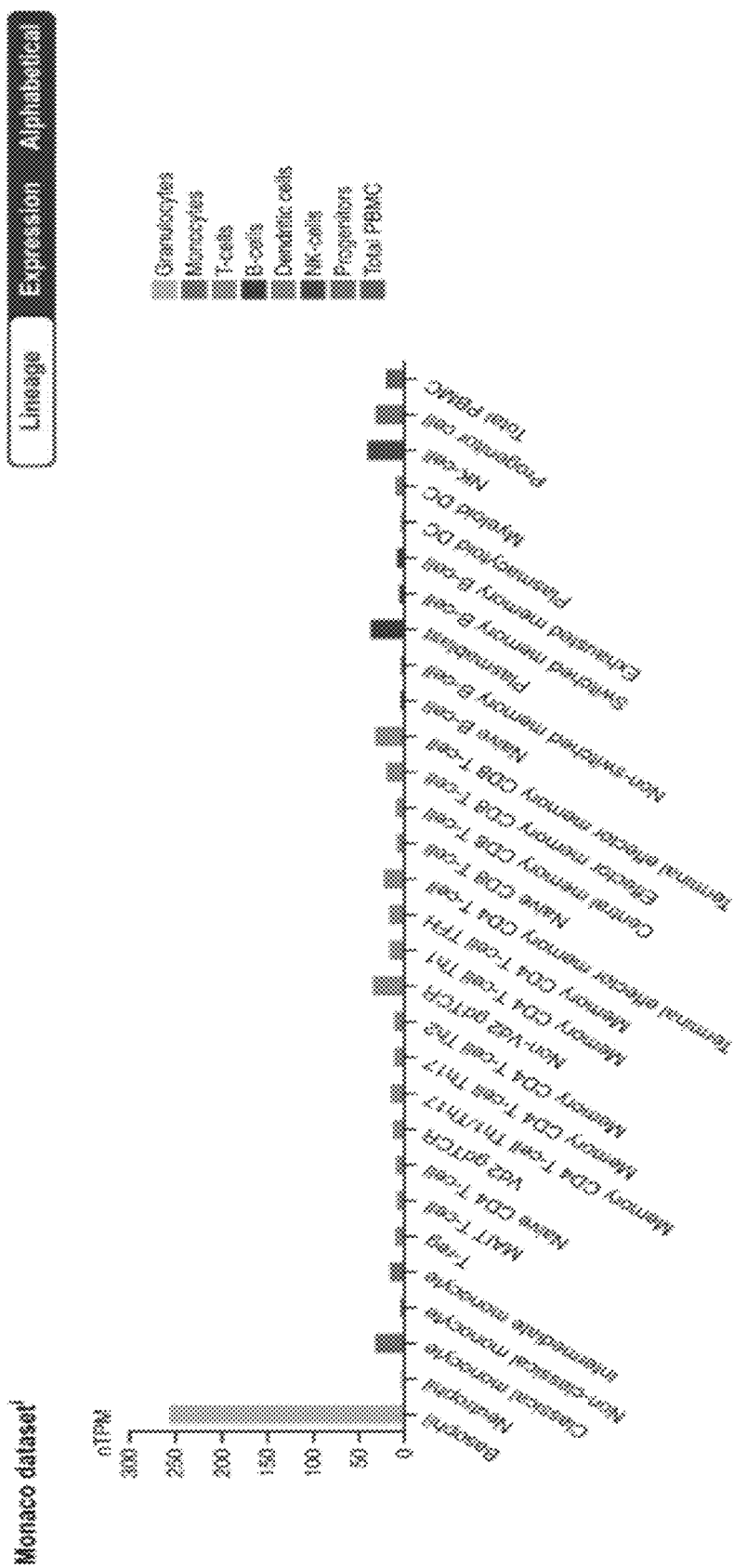
Figure 2C:
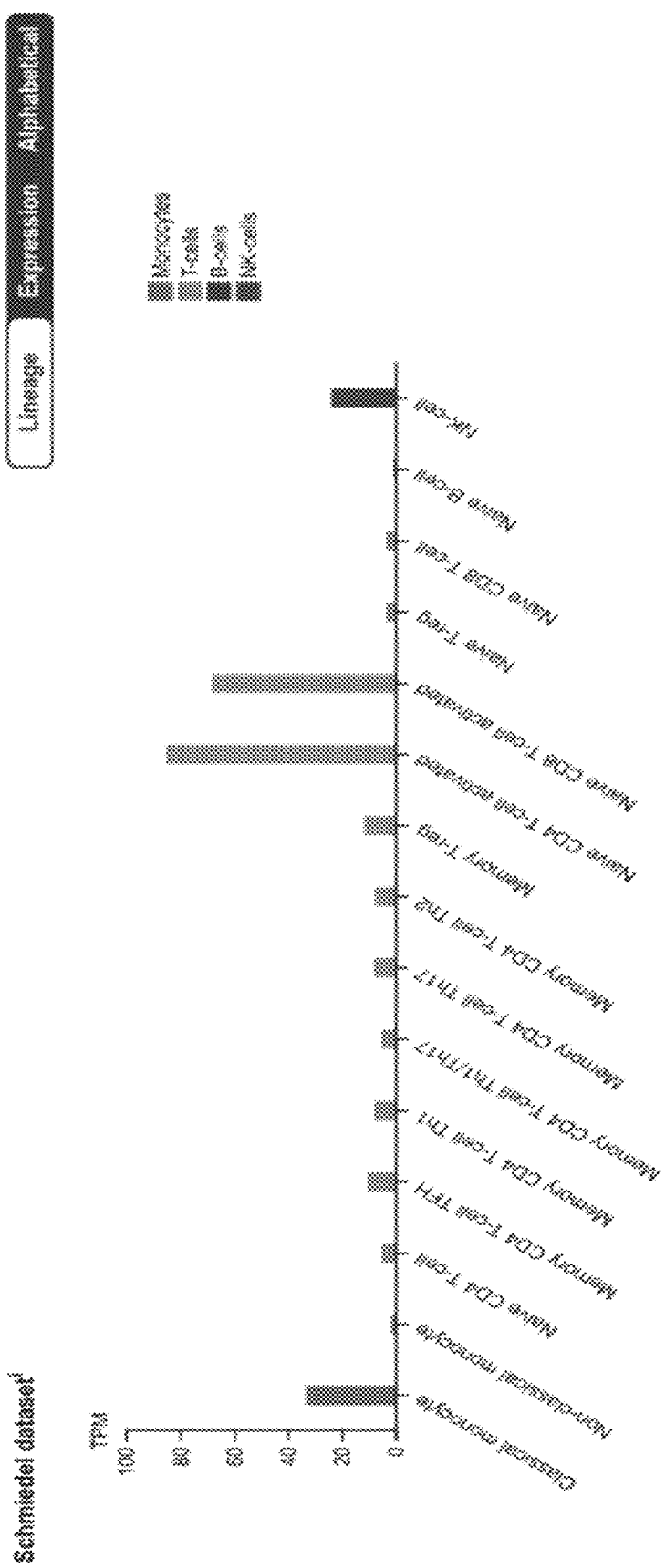
Figure 3A:
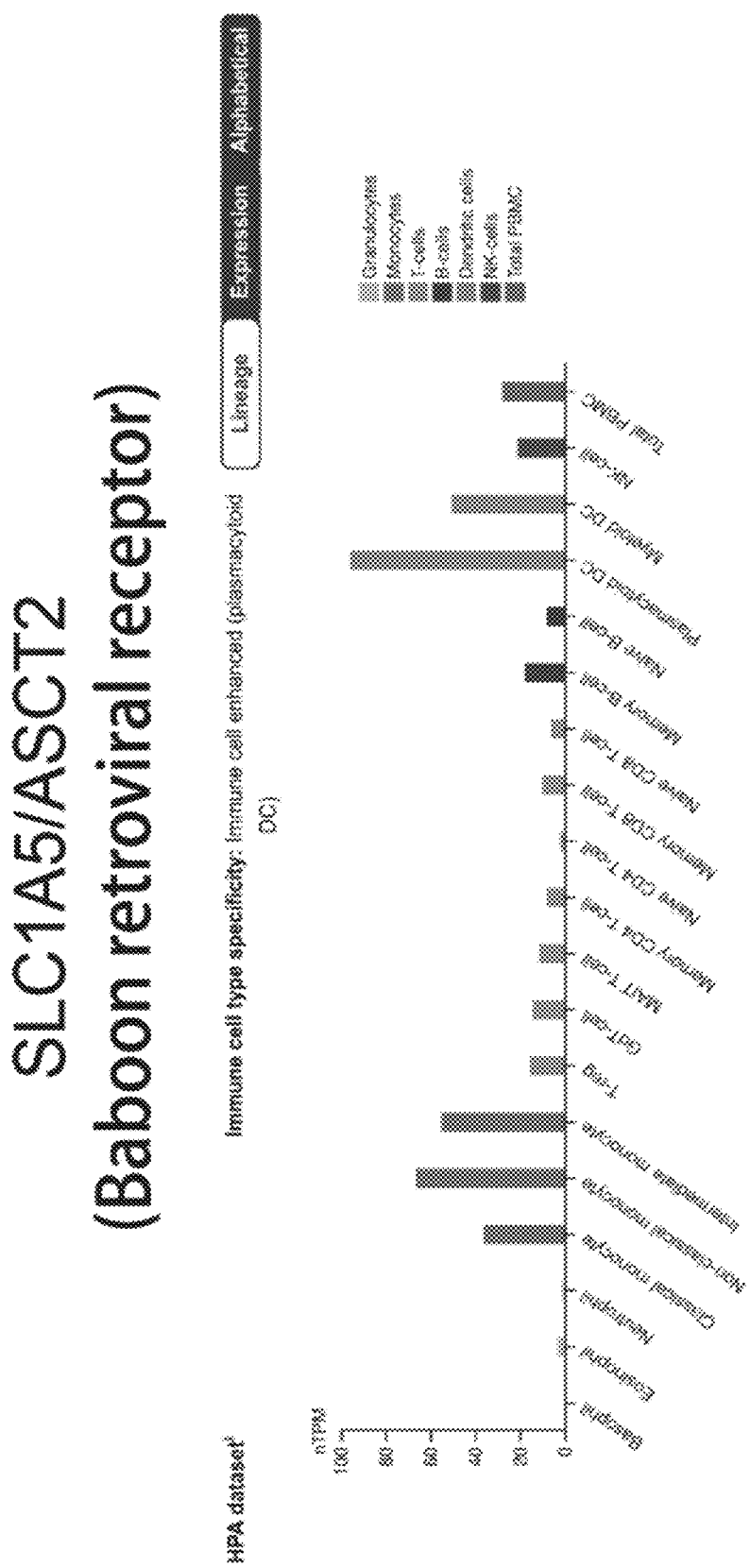
FIG. 3 is a graph showing the results of the analysis of the expression of SLC1A5 in blood cells.
Figure 3B:
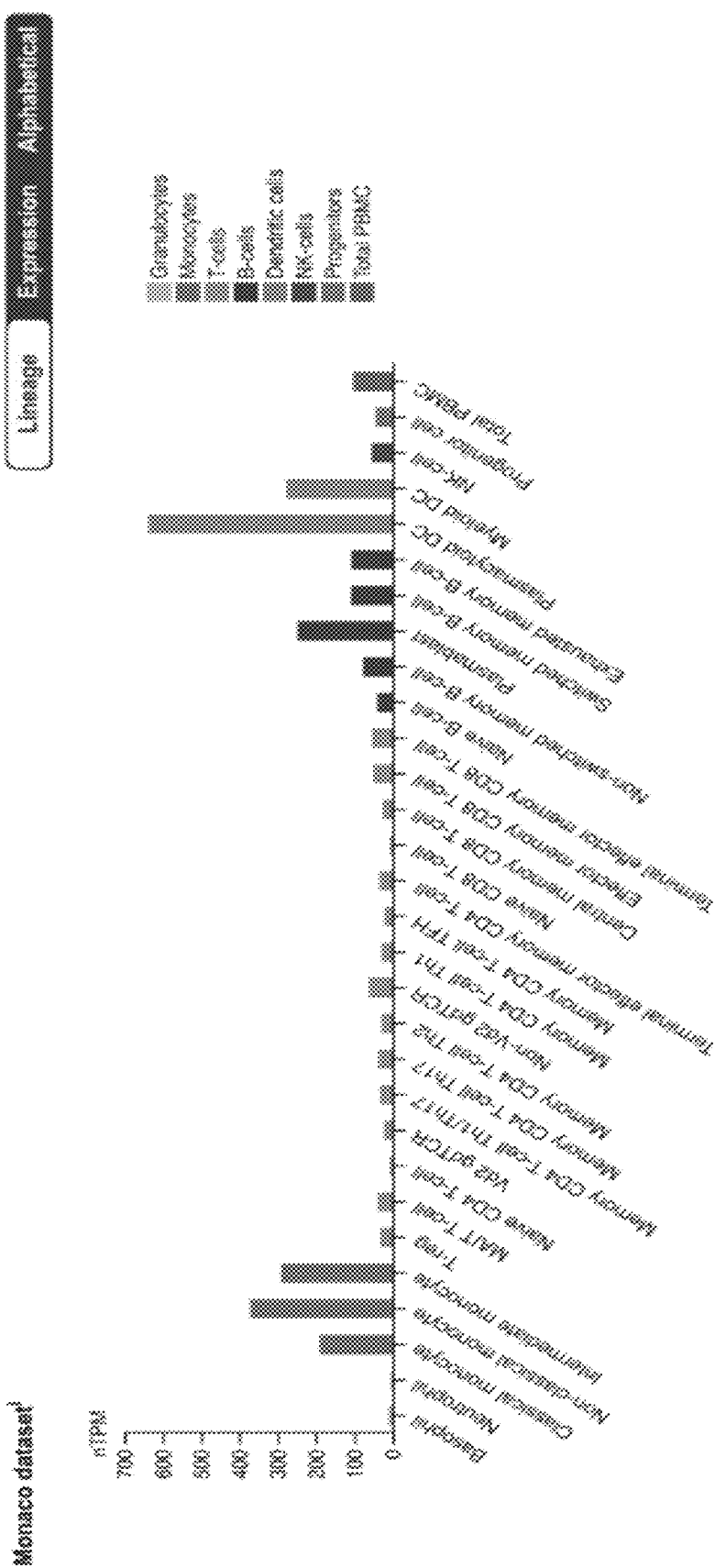
Figure 3C:
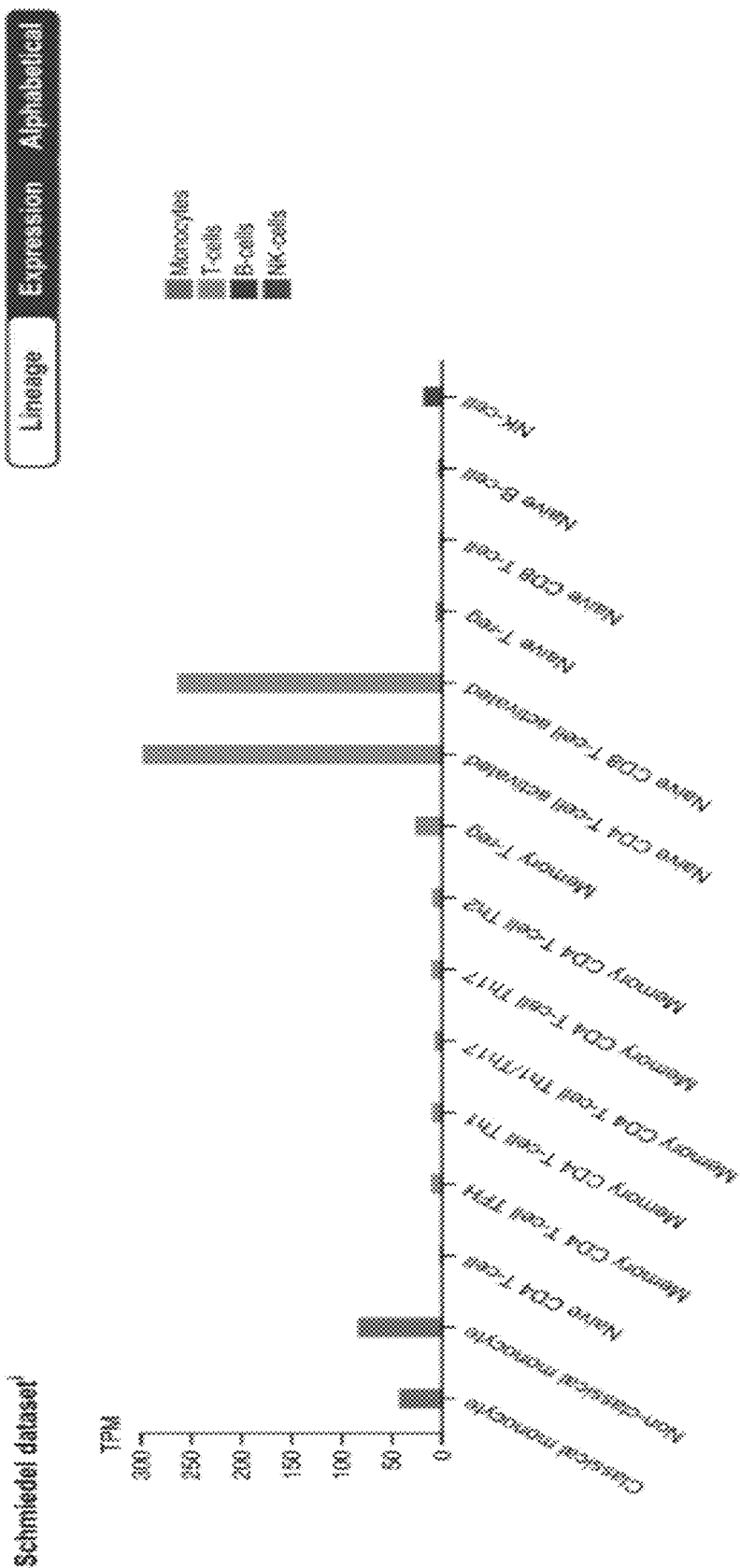
Figure 4:
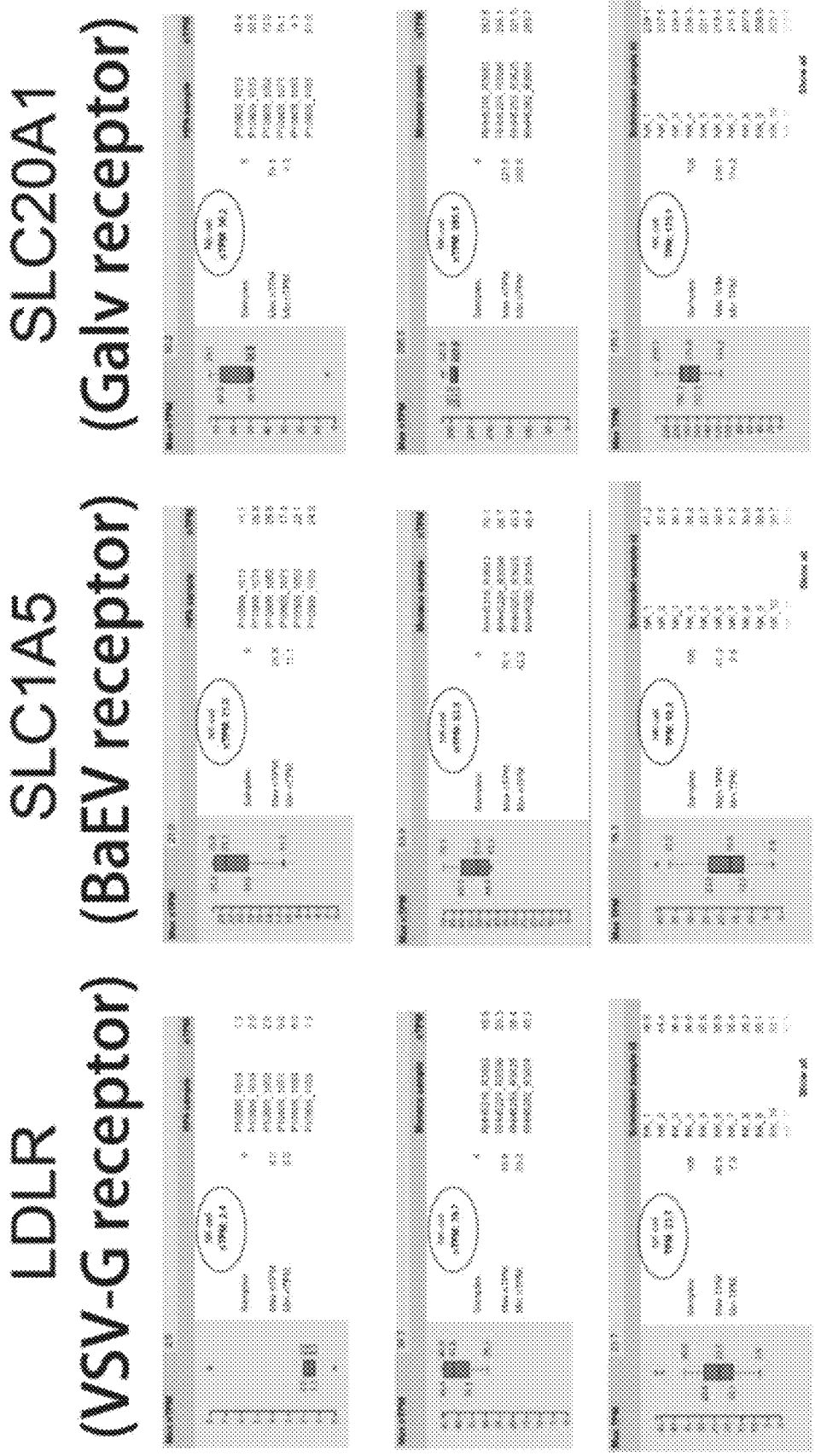
FIG. 4 is a graph showing the expression of LDLR, SLC1A5 and SLC20A1 on NK cells.

The present disclosure is further described below with reference to specific embodiments. The embodiments described below are merely preferred embodiments of the present disclosure and are not intended to limit the present disclosure in any other form. Any person skilled in the art may make equivalent embodiments by modifying the disclosed technical content in the same manner. Any simple modification or equivalent change made to the following embodiments based on the technical essence of the present disclosure without departing from the scope of the present disclosure is within the scope of protection of the present disclosure.

Universal Method-Steps for Preparation of Viral Liquid
1. HEK293T cells were prepared and cultured in a Dulbecco's modified eagle's medium (DMEM) with 10% serum until a convergence rate reached 80%.
2. A PEI solution (Shanghai Liji Biotechnology Co., Ltd., Cat: AC04L092) was used to mix with DNA at a volume-to-mass ratio of 3:1 to form a transfection complex. Four plasmids included an expression plasmid (containing a target gene intended for expression in the present disclosure), a packaging plasmid 1, a packaging plasmid 2, and an envelope plasmid, with a mass ratio of 2:1:1:1. The packaging plasmid 1 and the packaging plasmid 2 were derived from a Cell Biolabs VPK-206 viral transduction product.
3. After being placed at room temperature for 10-20 minutes, the transfection complex was added to HEK293T cells. After 12 hours, the transfection complex was removed, a DMEM with 5% serum was replaced with, followed by continuing to culture for 52 hours. Finally, a viral liquid was obtained and concentrated to measure biological titer, and then was store at −80 degrees.

Embodiment 1: Comparison of a Transduction System of the Present Disclosure with a Third-Generation Lentiviral Packaging System Using data from the proteinatlas.org database, the receptor expression of NK cells was analyzed, with the results shown in FIGS. 1-4. SLC20A1 was a receptor for GALV, LDLR was a receptor for a VSV-G envelope, and SLC1A5 was a Baboon retroviral (BaEV) receptor. The data in FIGS. 1-4 presented RNA-seq data and three separate multi-sample sequencing results. In the first row, which was derived from the sequencing of 6 samples, the RNA expression of SLC20A1 in NK cells was found to be at an average of 50.2 nTPM, the RNA expression of LDLR averaged 2.5 nTPM, and the RNA expression of SLC1A5 averaged 21 nTPM. The second row, derived from the sequencing of 4 samples, showed that the RNA expression of SLC20A1 in NK cells averaged 295 nTPM, the RNA expression of LDLR averaged 39.7 nTPM, and the RNA expression of SLC1A5 averaged 53 nTPM. The third row, derived from the sequencing of 105 samples, indicated that the RNA expression of SLC20A1 in NK cells averaged 175 nTPM, the RNA expression of LDLR averaged 23.7 nTPM, and the RNA expression of SLC1A5 averaged 18 nTPM.

Based on the data in FIGS. 1-4, it could be seen that the expression of GALV receptor (SLC20A1) was significantly higher than that of LDLR (VSV-G receptor), and significantly higher than that of BaEV receptor (SLC1A5), in all kinds of blood cells.

Figure 5:
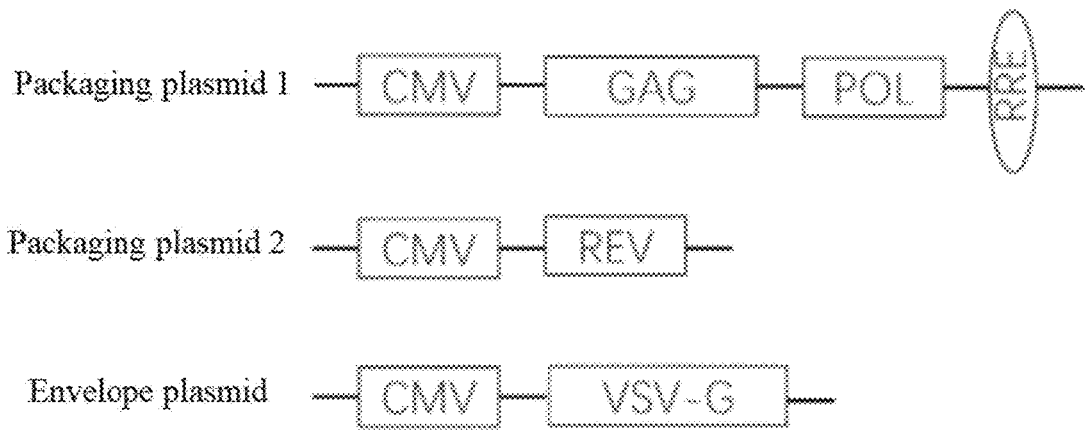
FIG. 5 is a schematic diagram comparing a viral system of the present disclosure with a conventional third-generation lentiviral packaging system.
Figure 5:
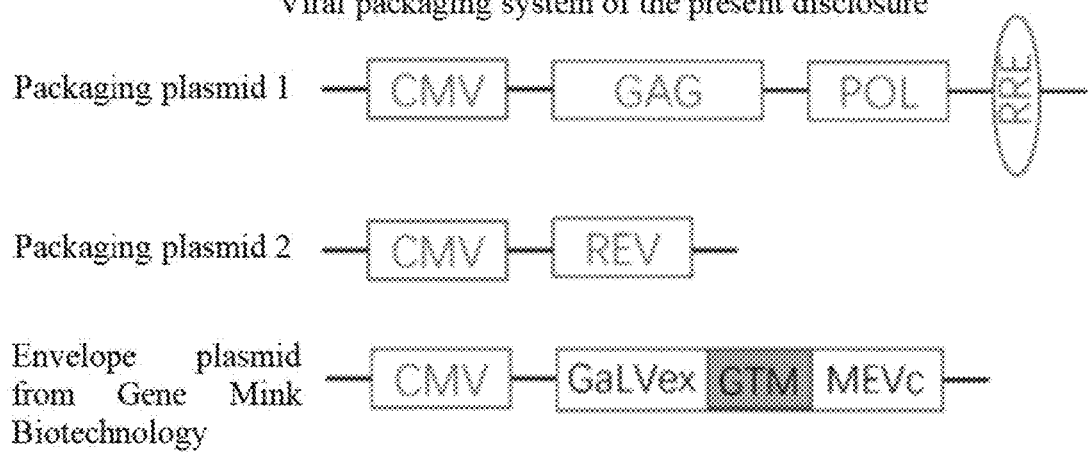

Therefore, SEQ ID NO.1-3 were sequentially ligated and constructed into the vector as the envelope plasmid of the viral transduction system of the present disclosure. A plasmid structure of the viral transduction system is shown in FIG. 5.

TABLE 1

Sequence of the protein QMV of the present disclosure

| Site | Name | Specific sequence | SEQ ID |
|---|---|---|---|
| Full length | Protein of the present disclosure (GalVex-GTM-MEVc) | MVLLPGSMLLTSNLHHLRHQMSPGSWKRLIILL SCVFGGGGTSLQNKNPHQPMTLTWQVLSQTGD VVWDTKAVQPPWTWWPTLKPDVCALAASLES WDIPGTDVSSSKRVRPPDSDYTAAYKQITWGAI GCSYPRARTRMASSTFYVCPRDGRTLSEARRCG GLESLYCKEWDCETTGTGYWLSKSSKDLITVK WDQNSEWTQKFQQCHQTGWCNPLKIDFTDKGK LSKDWITGKTWGLRFYVSGHPGVQFTIRLKITN MPAVAVGPDLVLVEQGPPRTSLALPPPLPPREAP PPSLPDSNSTALATSAQTPTVRKTIVTLNTPPPTT GDRLFDLVQGAFLTLNATNPGATESCWLCLAM GPPYYEAIASSGEVAYSTDLDRCRWGTQGKLTL TEVSGHGLCIGKVPFTHQHLCNQTLSINSSGDHQ YLLPSNHSWWACSTGLTPCLSTSVFNQTRDFCIQ VQLIPRIYYYPEEVLLQAYDNSHPRTKREAVSLT LAVLLGLGITAGIGTGSTALIKGPIDLQQGLTSLQ IAIDADLRALQDSVSKLEDSLTSLSEVVLQNRRG LDLLFLKEGGLCAALKEECCFYIDHSGAVRDSM KKLKEKLDKRQLERQKSQNWYEGWENNSPWFT TLLSTIAGPLLLLLLLLILGPCIINRLVQFVKDRIS VVQAL | — |
| 1-632 | Ex structure of GALV envelope glycoprotein | MVLLPGSMLLTSNLHHLRHQMSPGSWKRLIILL SCVFGGGGTSLQNKNPHQPMTLTWQVLSQTGD VVWDTKAVQPPWTWWPTLKPDVCALAASLES WDIPGTDVSSSKRVRPPDSDYTAAYKQITWGAI GCSYPRARTRMASSTFYVCPRDGRTLSEARRCG GLESLYCKEWDCETTGTGYWLSKSSKDLITVK WDQNSEWTQKFQQCHQTGWCNPLKIDFTDKGK LSKDWITGKTWGLRFYVSGHPGVQFTIRLKITN MPAVAVGPDLVLVEQGPPRTSLALPPPLPPREAP PPSLPDSNSTALATSAQTPTVRKTIVTLNTPPPTT GDRLFDLVQGAFLTLNATNPGATESCWLCLAM GPPYYEAIASSGEVAYSTDLDRCRWGTQGKLTL TEVSGHGLCIGKVPFTHQHLCNQTLSINSSGDHQ YLLPSNHSWWACSTGLTPCLSTSVFNQTRDFCIQ VQLIPRIYYYPEEVLLQAYDNSHPRTKREAVSLT LAVLLGLGITAGIGTGSTALIKGPIDLQQGLTSLQ IAIDADLRALQDSVSKLEDSLTSLSEVVLQNRRG LDLLFLKEGGLCAALKEECCFYIDHSGAVRDSM KKLKEKLDKRQLERQKSQNWYEGWENNSPWFT TLL | 1 |
| 633-653 | TM structure of GALV | STIAGLLLLLLLLILGPCII | 2 |
| 654-670 | MEVc | NRLVQFVKDRISVVQAL | 3 |

Figure 6:
FIG. 6 is a schematic structural diagram of a CAR expressing BCMA antibodies.

According to the method in the universal method, viral liquids of the viral system of the present disclosure and the third-generation lentiviral packaging system were prepared, and NK cells were transduced. The target gene was a CAR structure expressing a BCMA antibody (structural diagram shown in FIG. 6).

NK cells were derived from peripheral blood monocular cells (PBMC), and 8 μg/mL of polybrene was added along with 10 MOI of a virus. After 16 hours, a fresh NK cell culture medium was added to remove a medium containing the virus.

After being infected with the virus, NK cells were taken out for detecting cell viability and positive rates on days 3, 6, 9, and 15. Specifically, 0.5 of E6NK cells were taken and washed twice with phosphate buffered saline (PBS), followed by adding 100 μL of magnetic-activated cell sorting (MACS) buffer, and adding 1 μL of BCMA ScFv-specific recognition reagent (Miltenyi order #: 130-126-090). After that, the E6NK cells were incubated at room temperature for 10 minutes, and then washed twice. The BCMA-positive cell ratio was detected using a flow cytometry.

Experimental Results

Figure 7A:
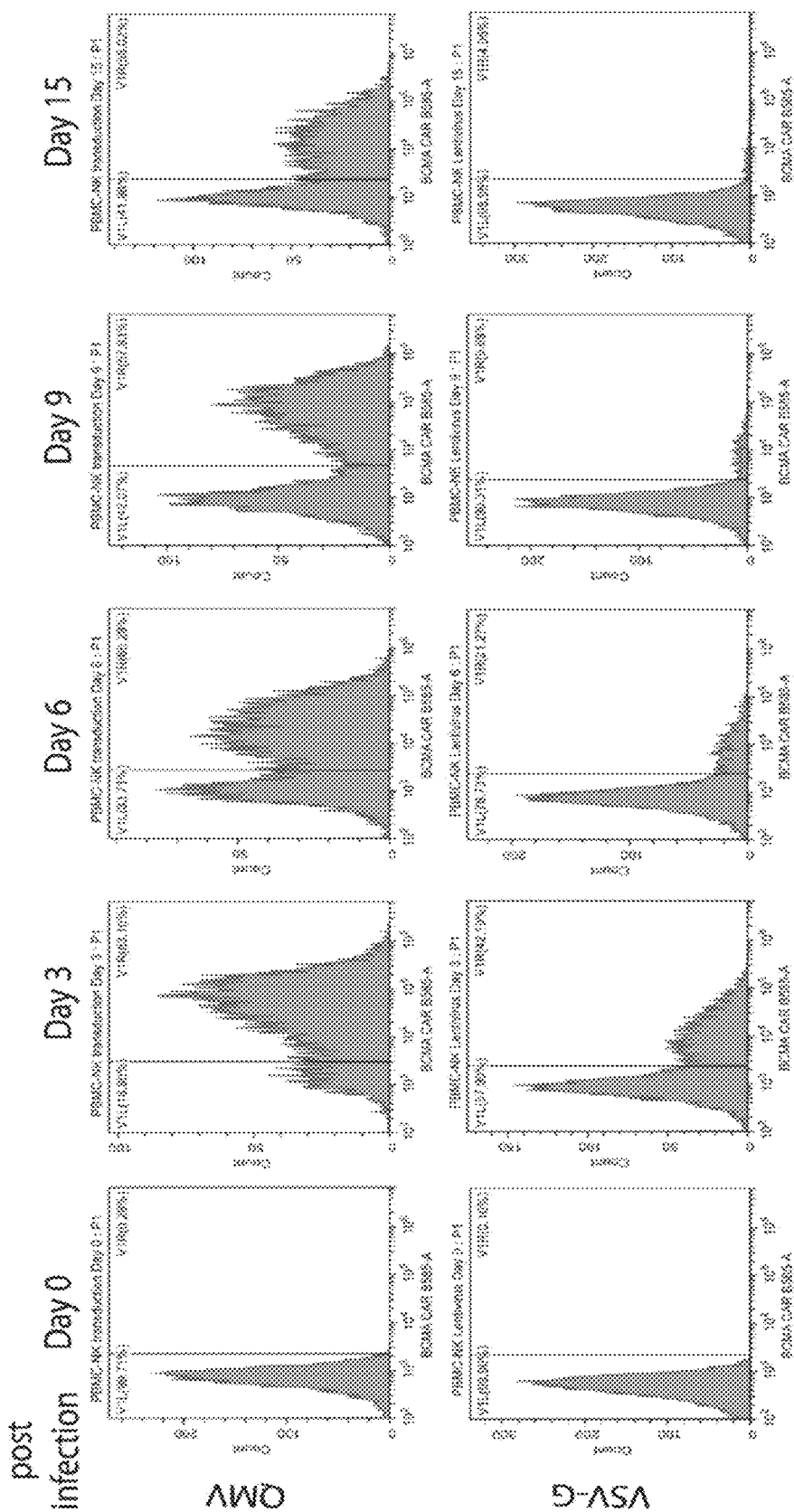
FIG. 7A shows the results of the CAR+ positive rates detected by a flow cytometry on days 3, 6, 9, and 15.
Figure 7B:
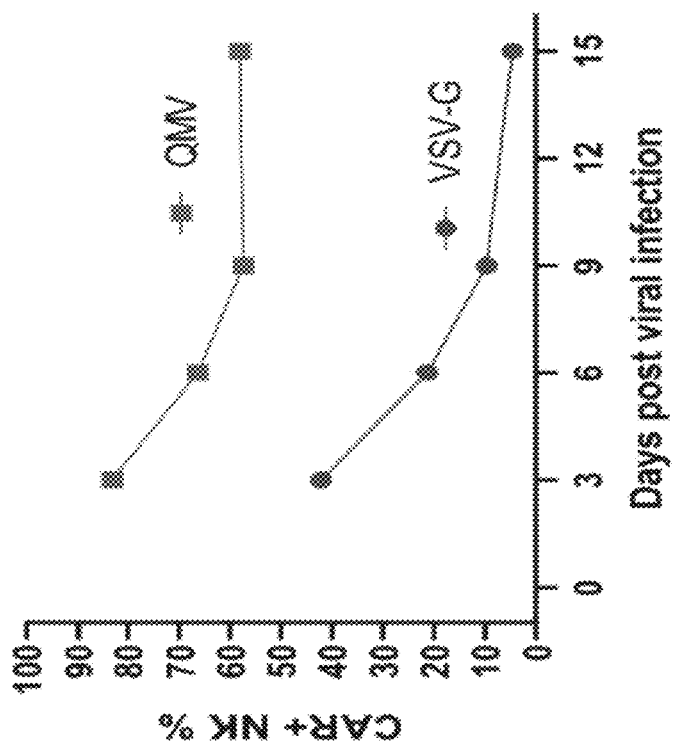
FIG. 7B presents the change curves for the CAR+ positive rates on days 3, 6, 9, and 15. It can be seen that the positive rate for cells infected with QMV virus is above 80% on day 3, drops to around 65% on day 6, and stabilizes at over 50% after day 9. In contrast, the positive rate for cells infected with VSVG virus declines rapidly, with 40% on day 3, dropping to 20% on day 6, 10% on day 9, and reaching 5% on day 15.

FIGS. 7A and 7B show that the positive rate of cells infected with QMV virus is over 80% on the third day, drops to around 65% on the sixth day, and stabilizes above 50% after the ninth day. In contrast, the positive rate of cells infected with VSV-G virus declines rapidly, with a positive rate of 40% on the third day, dropping to 20% on the sixth day, 10% on the ninth day, and 5% on the fifteenth day.

Figure 7C:
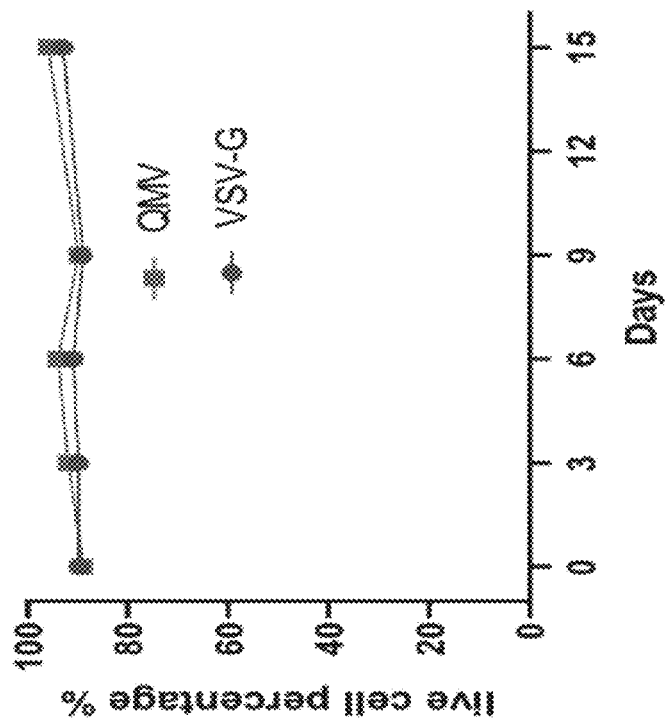
FIG. 7C displays the cell viability on days 3, 6, 9, and 15, showing no significant differences in cell viability between cells infected with QMV and VSVG at the aforementioned time points.
Figure 8A:
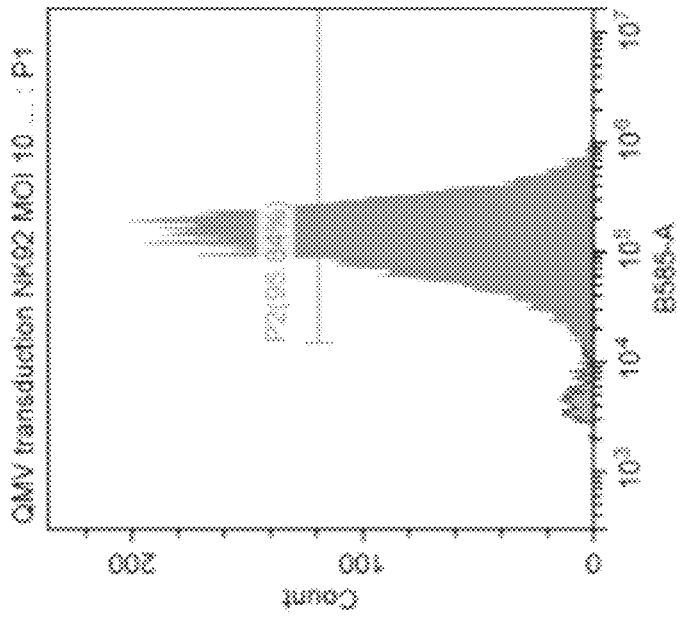
FIG. 8 is a graph showing detection results for positive rates after transduction of CAR to NK cells or T cells using the viral system of the present disclosure versus the conventional third-generation lentiviral packaging system.
Figure 8A:
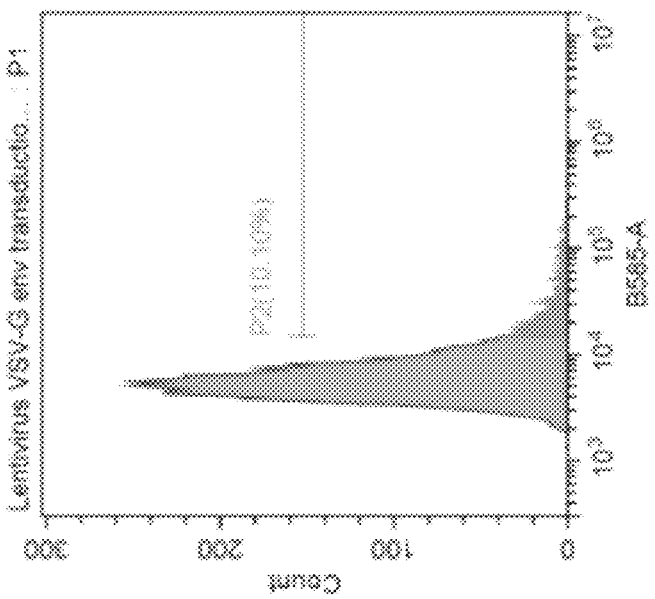
Figure 8B:
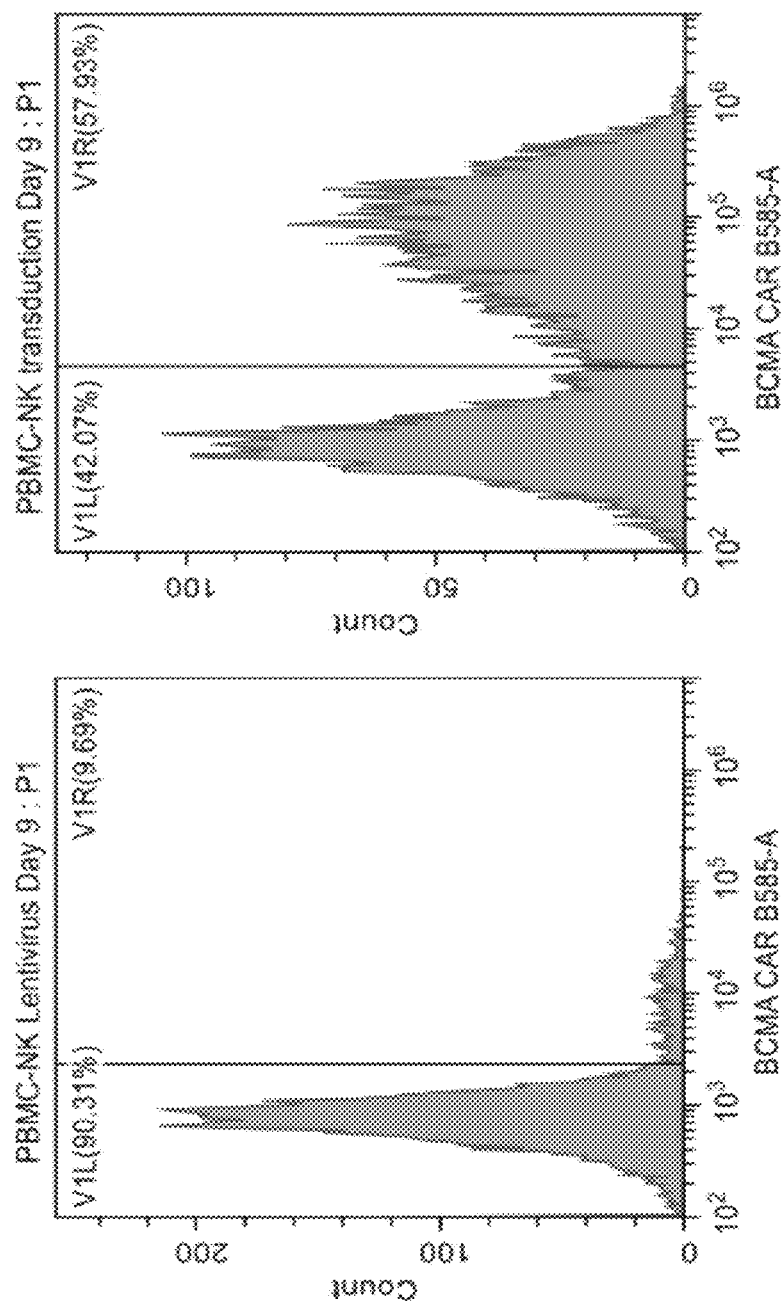
Figure 8C:
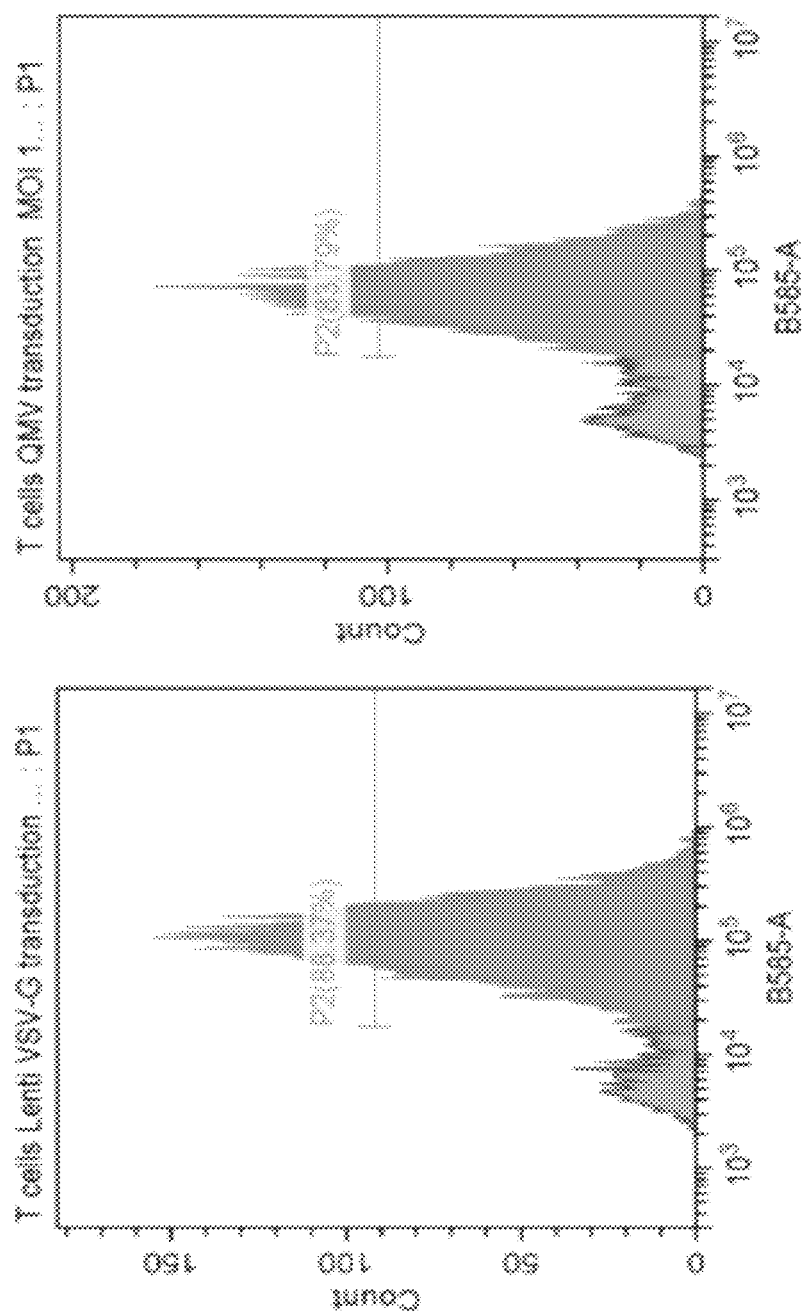

Simultaneously, cell viability is monitored on days 3, 6, 9, and 15. The cell viability of both QMV and VSV-G infected cells remains unchanged after 15 days of culture, as shown in the statistics in FIG. 7C.

Embodiment 2: Comparison of Transfection of CAR and GFP into NK Cells and T Cells To determine whether the QMV virus was CAR-specific and NK cell-specific, further comparative experiments were conducted.

Using the method described in Embodiment 1, VSV-G and QMV viruses were used to transduce BCMA-CAR into PB-NK, NK92, and T cells. The positive rates were detected on the ninth day post-transduction, using the same detection method as in Embodiment 1. As shown in FIG. 8, the BCMA-CAR positive rates for NK92 and PB-NK cells infected with VSV-G were around 10%, while the BCMA-CAR positive rates for NK92 and PB-NK cells infected with QMV were approximately 95% and 60%, respectively. For T cells infected with VSV-G and QMV viruses, the BCMA-CAR positive rates were similar, around 83%.

Figure 9A:
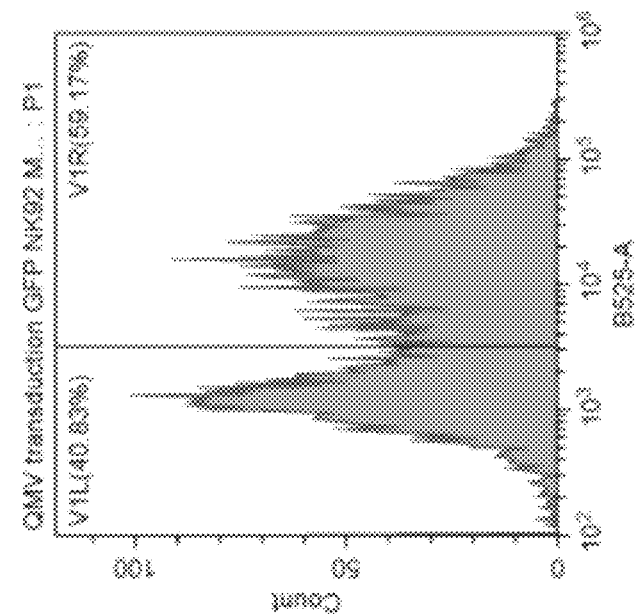
FIG. 9 is a graph showing assay results for the positive rates after transduction of green fluorescent protein (GFP) into NK cells or T cells using the viral system of the present disclosure versus the conventional third-generation lentiviral packaging system.
Figure 9B:
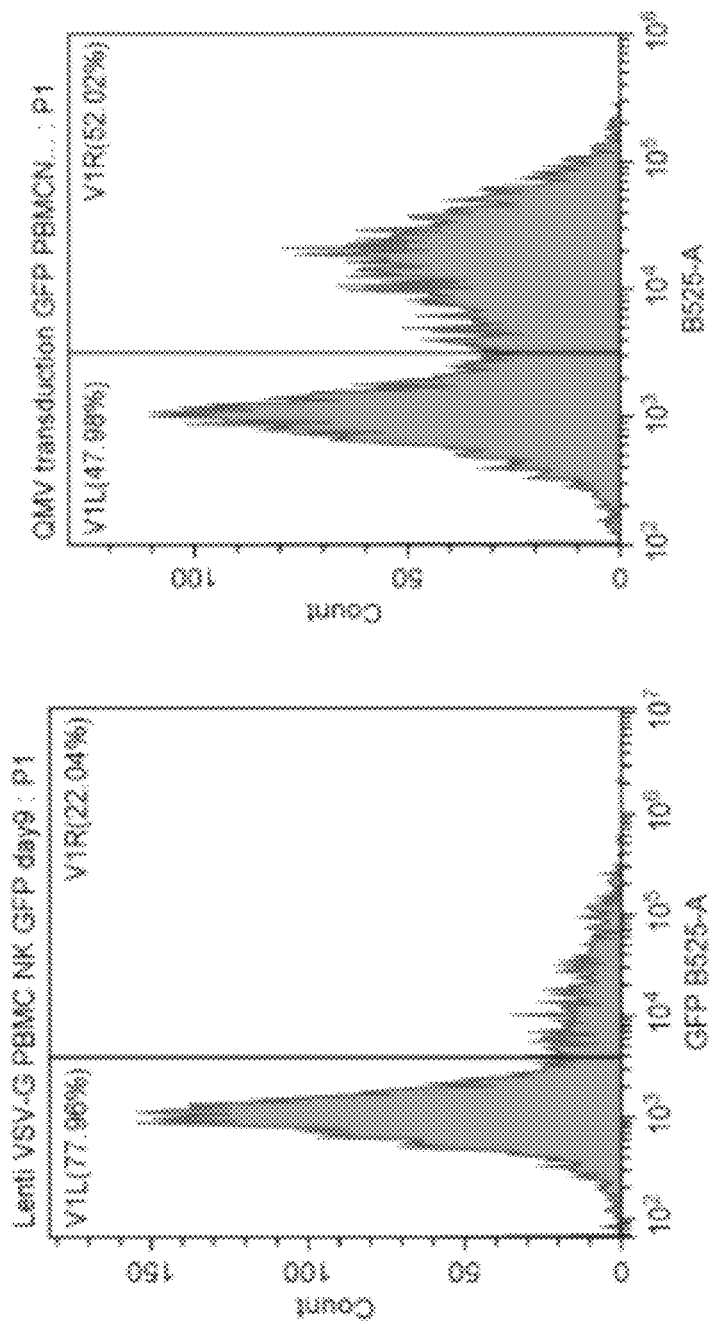
Figure 9C:
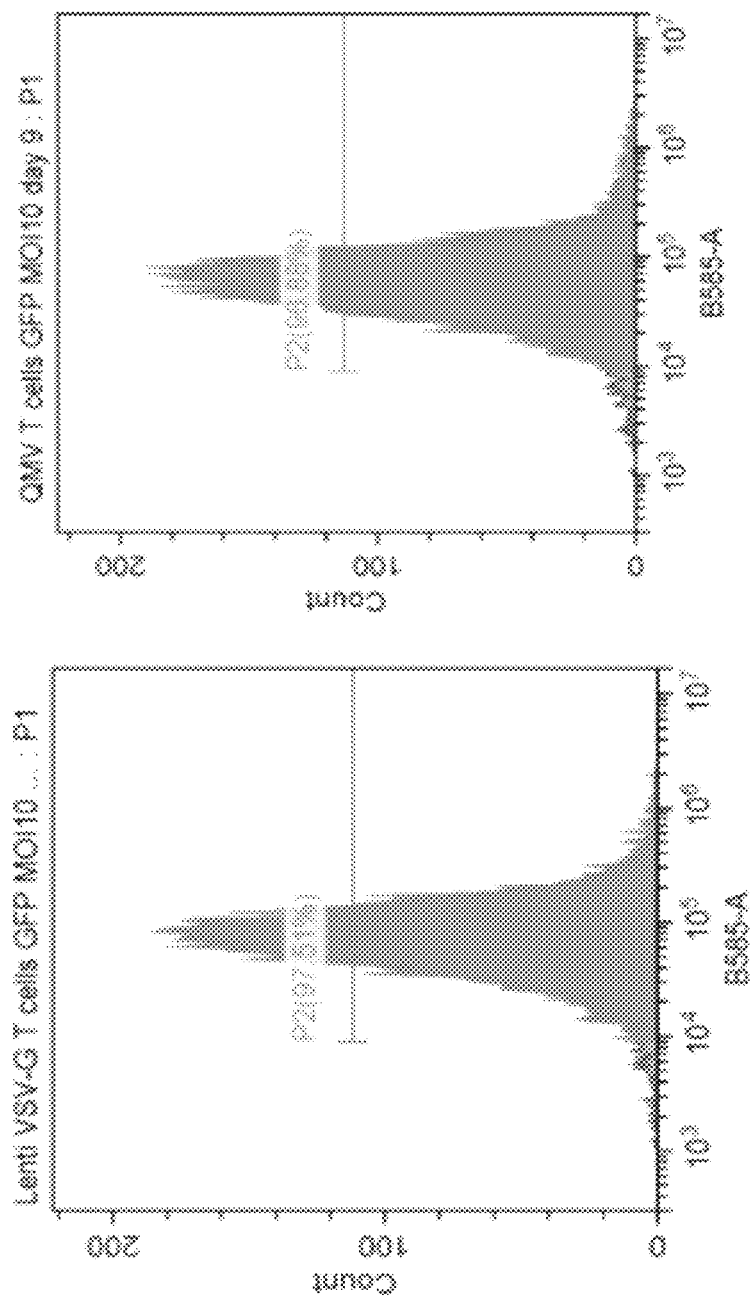

Following the same method as in Embodiment 1, VSV-G and QMV viruses were used to transduce GFP into PB-NK, NK92, and T cells, with the positive rates detected on the ninth day post-transduction, using the same detection method as in Embodiment 1. As shown in FIG. 9, the GFP positive rates for NK92 and PB-NK cells infected with VSV-G were 36% and 22%, respectively, while the GFP positive rates for NK92 and PB-NK cells infected with QMV were 60% and 50%, respectively. For T cells infected with VSV-G and QMV viruses, the GFP positive rates were similar, both in the range of 96-97%.

The above results indicate that the QMV viral transduction system of the present disclosure is suitable for various immune cells, demonstrating high and stable transduction efficiency when expressing different target genes.

The invention claimed is:

1. A method for preparing natural killer (NK) cells expressing a target gene, comprising the steps of transfecting cells with a vector composition containing an envelope plasmid, collecting a viral liquid, and contacting the viral liquid with NK cells, the envelope plasmid encoding a fusion protein having an X-Y-Z structure, the X having an amino acid sequence as shown in SEQ ID NO. 1, the Y having an amino acid sequence as shown in SEQ ID NO.2, and the Z having an amino acid sequence as shown in SEQ ID NO.3, wherein the envelope plasmid is configured to cause expression of the fusion protein in the transfected cells, wherein the vector composition further contains the following plasmids:

1) An expression plasmid containing a sequence encoding a target gene, wherein the expression plasmid is configured to cause expression of the target gene in the transfected cells,
2) a packaging plasmid 1 containing a sequence encoding specific antigen (GAG), or polymerase (POL), or a combination thereof, wherein the expression plasmid is configured to cause expression said GAG, said POL, or said combination thereof in the transfected cells; and
3) A packaging plasmid 2 containing a sequence encoding a regulator of expression of virion protein (REV), wherein the expression plasmid is configured to cause expression of the REV in the transfected cells; and wherein the fusion protein is QMV, which forms a pseudovirus named QMV virus targeting a receptor SLC20A1.

2. The method according to claim 1, wherein the expression plasmid, the packaging plasmid 1, the packaging plasmid 2 and the envelope plasmid are in a mass ratio of 2:1:1:1.

3. The method according to claim 1, wherein the packaging plasmid 1, the packaging plasmid 2, and the envelope plasmid each independently comprises a cytomegalovirus (CMV) promoter.

4. NK cells prepared by a method according to claim 1.

5. NK cells according to claim 4, wherein the NK cells are human cells.

6. NK cells according to claim 4, wherein the target gene encodes an antibody, a chimeric antigen receptor (CAR) or a functional protein.

7. NK cells according to claim 6, wherein the antibody and the CAR target any one or more of the following sites: BCMA, CD19, CD20, CD123, CD22, CD3D, CD3E, CD7CLEC12AGPRC5D, CD138, CD30, CD33, CD38, CD3E, CD79BSLAMF7, CD10, CD117, CD37, CD4, CD5, CD56, CD72, CD79A, CD99, Flt-3, LILRA3, LILRB4, SLAMF3, Her2, MSLN, B7-H3, CLDN18, EGFR, GPC3, KRAS, CA9, CEA, EGFRVIII, EphA2, ERBB3, ERBB4, FAP, GUCY2C, IL13RA2, MUC1, PD-1, PSMA, VEGFR2, AFP, AXL, CD133, CD147, CD171, CD80, CD86, c-Met, DLL4, EpCAM, Nectin-4, Podoplanin, ROBO1, ROR2, SSTR2, FOLR1, ROR1, CD70, NKG2D, PD-L1, and SIRP alpha.

* * * * *

SEQUENCE LISTING

```
Sequence total quantity: 3
SEQ ID NO: 1             moltype = AA  length = 632
FEATURE                  Location/Qualifiers
source                   1..632
                         mol_type = protein
                         organism = synthetic construct
SEQUENCE: 1
MVLLPGSMLL TSNLHHLRHQ MSPGSWKRLI ILLSCVFGGG GTSLQNKNPH QPMTLTWQVL  60
SQTGDVVWDT KAVQPPWTWW PTLKPDVCAL AASLESWDIP GTDVSSSKRV RPPDSDYTAA 120
YKQITWGAIG CSYPRARTRM ASSTFYVCPR DGRTLSEARR CGGLESLYCK EWDCETTGTG 180
YWLSKSSKDL ITVKWDQNSE WTQKFQQCHQ TGWCNPLKID FTDKGKLSKD WITGKTWGLR 240
FYVSGHPGVQ FTIRLKITNM PAVAVGPDLV LVEQGPPRTS LALPPPLPPR EAPPPSLPDS 300
NSTALATSAQ TPTVRKTIVT LNTPPPTTGD RLFDLVQGAF LTLNATNPGA TESCWLCLAM 360
GPPYYEAIAS SGEVAYSTDL DRCRWGTQGK LTLTEVSGHG LCIGKVPFTH QHLCNQTLSI 420
NSSGDHQYLL PSNHSWWACS TGLTPCLSTS VFNQTRDFCI QVQLIPRIYY YPEEVLLQAY 480
DNSHPRTKRE AVSLTLAVLL GLGITAGIGT GSTALIKGPI DLQQGLTSLQ IAIDADLRAL 540
QDSVSKLEDS LTSLSEVVLQ NRRGLDLLFL KEGGLCAALK EECCFYIDHS GAVRDSMKKL 600
KEKLDKRQLE RQKSQNWYEG WFNNSPWFTT LL                              632

SEQ ID NO: 2             moltype = AA  length = 21
FEATURE                  Location/Qualifiers
source                   1..21
                         mol_type = protein
                         organism = synthetic construct
SEQUENCE: 2
STIAGPLLLL LLLLILGPCI I                                           21

SEQ ID NO: 3             moltype = AA  length = 17
FEATURE                  Location/Qualifiers
source                   1..17
                         mol_type = protein
                         organism = synthetic construct
SEQUENCE: 3
NRLVQFVKDR ISVVQAL                                                17
```